US 7,507,952 B2

(12) United States Patent
Groves et al.

(10) Patent No.: US 7,507,952 B2
(45) Date of Patent: Mar. 24, 2009

(54) APPARATUS AND METHOD FOR FLUID DENSITY DETERMINATION (75) Inventors: Joel Lee Groves, Leonia, NJ (US); Etienne Vallee, Princeton, NJ (US); Peter Wraight, Skillman, NJ (US)

(73) Assignee: Schlumberger Technology Corporation, Sugar Land, TX (US)

( * ) Notice: Subject to any disclaimer, the term of this patent is extended or adjusted under 35 U.S.C. 154(b) by 250 days.

(21) Appl. No.: 11/308,910

(22) Filed: May 25, 2006

(65) Prior Publication Data

US 2007/0274443 A1    Nov. 29, 2007

(51) Int. Cl.
*G01V 5/08* (2006.01)
(52) U.S. Cl. .................................. 250/269.1
(58) Field of Classification Search .............. 250/269.1, 250/269.2, 269.3, 269.4, 269.5, 269.6, 269.7, 250/269.8
See application file for complete search history.

(56) References Cited

U.S. PATENT DOCUMENTS

| 2,986,639 | A | * | 5/1961 | Josendal et al. ............. 250/254 |
| 3,103,812 | A | * | 9/1963 | Bourne, Jr. et al. ....... 73/152.42 |
| 3,529,151 | A | | 9/1970 | Carr-Brion |
| 4,490,609 | A | | 12/1984 | Chevalier |
| 4,956,859 | A | | 9/1990 | Lanza et al. |
| 5,651,041 | A | | 7/1997 | Moller et al. |
| 5,680,431 | A | | 10/1997 | Pietras, III et al. |
| 5,712,890 | A | * | 1/1998 | Spivey et al. ................. 378/37 |
| 2003/0106993 | A1 | * | 6/2003 | Chen et al. ............... 250/269.1 |
| 2005/0031074 | A1 | | 2/2005 | Fitzgerald |
| 2006/0067473 | A1 | * | 3/2006 | Eberhard et al. ........... 378/98.9 |
| 2007/0138399 | A1 | | 6/2007 | Simonetti et al. |

FOREIGN PATENT DOCUMENTS

| DE | 26 49 512 A1 | 5/1978 |
| EP | 0499975 A1 | 8/1992 |

* cited by examiner

*Primary Examiner*—David P Porta
*Assistant Examiner*—Kiho Kim
(74) *Attorney, Agent, or Firm*—Darla P. Fonseca; Jaime Castano (57) ABSTRACT A fluid density determination apparatus and method comprising an X-ray generator emitting a high energy radiation signal and a low energy radiation signal; a sample cell housing a sample of interest and at least one of the high energy and low energy radiation signals being directed through the sample cell; and a radiation detector measuring the output radiation from the sample cell. Data gathered at the radiation detector using the high and low energy signals are used to calculate the density of the fluid sample of interest.

33 Claims, 7 Drawing Sheets

APPARATUS AND METHOD FOR FLUID DENSITY DETERMINATION

FIELD OF THE INVENTION

The present invention relates to the field of density determination of fluid samples of interest. More particularly, the present invention is directed to apparatus and methods that utilize x-rays to determine fluid density in oilfield exploration and development.

BACKGROUND OF THE INVENTION

Co-owned United States patent application publication number US 2003/0106993 by Chen et al., which is hereby incorporated by reference herein in its entirety, discloses use of nuclear electromagnetic irradiation for density determination. In this, knowing the density of a sample of interest, for example, a fluid in a borehole, can provide important information to end users. For example, dead crude oil (i.e., oil at the formation surface and at ambient pressure) consists primarily of carbon and hydrogen with some contaminants or unwanted elements such as sulfur which constitute by weight a few percent of the oil. Generally the economic value of the crude oil increases with its hydrogen content compared to its carbon content. Asphaltenes are primarily large, aromatic molecules of considerable densities. Thus, in crude oil, a high density is generally indicative of high asphaltene content. The presence of a large amount of asphaltenes in oil is undesirable from both a production viewpoint and from a processing perspective. In production, asphaltenes are known to plug oil wells.

The measurement of fluid density, in conditions encountered downhole, is a service that is desired in the oilfield exploration and development industry. A nuclear based measurement is one reliable and rugged way to obtain the density from a large variety of fluids. Optical techniques currently used for the analysis of downhole fluid samples are not sufficient to completely characterize the downhole fluids drawn into sampling devices. Mixtures of several different liquids are likely to be found in formation fluids causing difficulties in optical measurements. Two fluids may have the same density but different optical absorption characteristics. One example is a heavy oil precipitating asphaltene from solution, the average density of the fluid is unchanged as the precipitate forms, but the optical properties of the fluid are dramatically affected.

One technique for measuring fluid density that overcomes this limitation of optical techniques is a photon attenuation measurement, in which the attenuation of gamma ray photons passing transversely through a pipe containing a fluid is measured. However, this technique is intended for use in locations where spatial constraints are not too severe. In deep boreholes of relatively small diameter, and in certain borehole tools, the space available for the apparatus required for such a measurement can be limited.

In addition to the failure to provide for a small space measurement, previous attempts to measure density downhole have utilized a chemical radiation source that carries high liability and operating requirements. Using a chemical radiation source introduces other concerns as well. Due to the danger associated with these sources, it is necessary to use a source with a low intensity to meet stringent regulations. This low intensity source requires both longer measurement times and a larger flow line that may not fit in the constraints down hole.

BRIEF SUMMARY OF THE INVENTION

In consequence of the background discussed above, and other factors that are known in the field of formation fluid analysis, applicants recognized a need for improved apparatus and methods for determining density of fluid samples in rugged and harsh conditions, such as the conditions typically found in oilfield environments. Applicants further recognized that an apparatus was needed that could be used in environments posing size constraints, such as in a borehole, and be able to withstand the high temperature and noise environments encountered downhole. Additionally, applicants recognized that an x-ray generator could be used along with one or more radiation detectors to provide a reliable measure of sample fluid density, downhole or at a surface location in an oilfield-type environment.

One embodiment comprises a method and apparatus for determining the density of a fluid downhole. In one aspect, an x-ray generator provides radiation input that is filtered at different times by one high energy filter and one low energy filter. The filtered radiation is introduced to two channels, one housing a sample fluid and routed to a first radiation detector and the other routed to a second radiation detector. The measurements of the two radiation detectors are used in analysis to determine the density of the sample fluid and provide insight regarding its composition.

Additional advantages and novel features of the invention will be set forth in the description which follows or may be learned by those skilled in the art through reading the materials herein or practicing the invention. The advantages of the invention may be achieved through the means recited in the attached claims.

BRIEF DESCRIPTION OF THE DRAWINGS

The accompanying drawings illustrate embodiments of the present invention and are a part of the specification. Together with the following description, the drawings demonstrate and explain principles of the present invention.

DETAILED DESCRIPTION

Illustrative embodiments and aspects of the invention are described below. In the interest of clarity, not all features of an actual implementation are described in the specification. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such development effort might be complex and time-consuming, but would nevertheless be a routine undertaking for those of ordinary skill in the art having benefit of the disclosure herein.

Figures 1A, 1B:
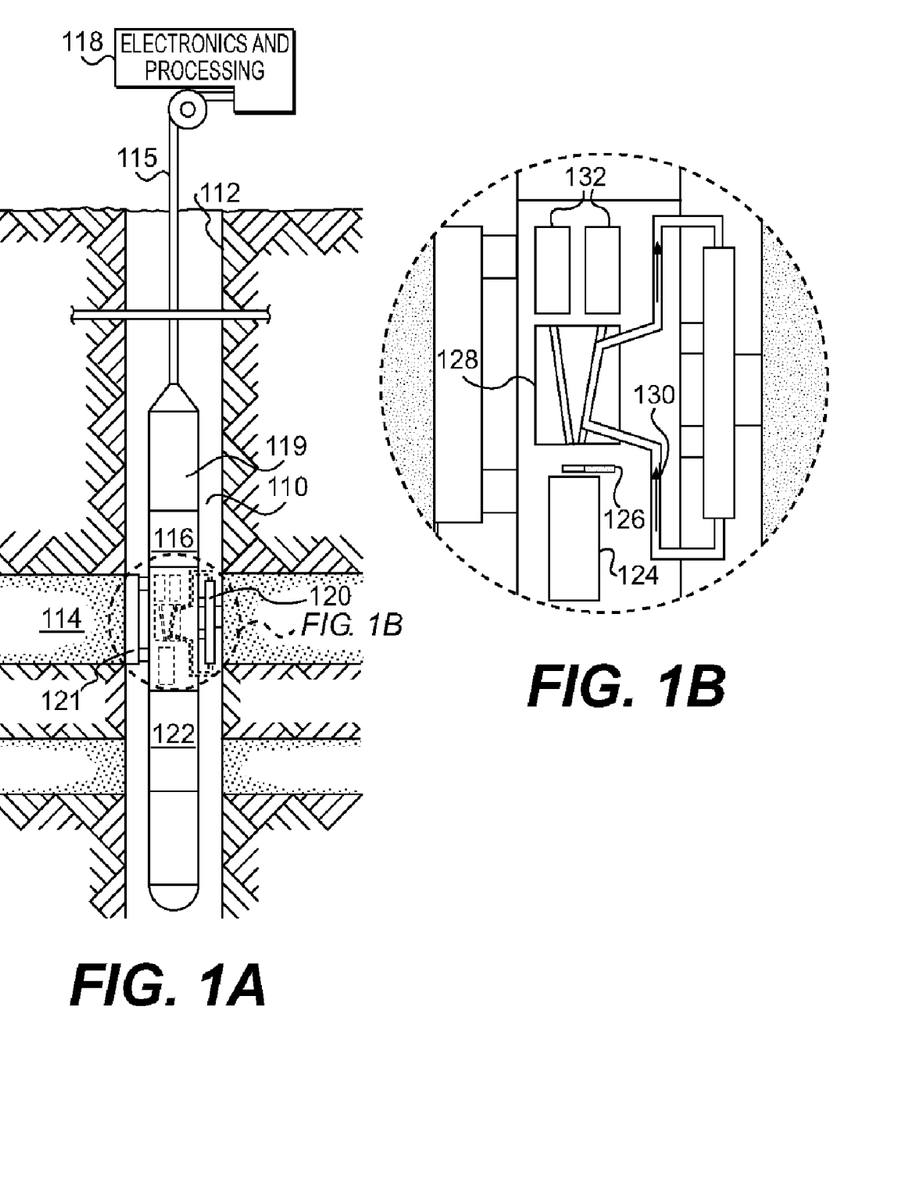
FIG. 1A is a schematic view of one operating environment for apparatus and methods of the present invention.
FIG. 1B is an expanded schematic view of a portion of one system for measuring density of fluid material within a borehole.

Referring now to the drawings and particularly to FIGS. 1A and 1B, there is shown a schematic illustration of one possible operational context of the instant invention. For instance, it will be understood that instead of being deployed on a wireline tool, the methods and apparatus disclosed herein could be deployed on slickline, in a logging-while-drilling collar, on coiled tubing, as part of permanent or semi-permanent completion hardware, or as a part of oilfield infrastructure such as pipelines.

In FIG. 1A, borehole tool 110 is shown for analyzing gases, fluids, and other materials from a formation 114. One instance of this type of borehole tool is the Modular Dynamics Tester (MDT), a trademark of Schlumberger. The tool 110 is suspended in the borehole 112 from the lower end of a cable 115. The cable 115 is anchored onto and lowered from the surface of the borehole. On the surface, cable 115 is electrically coupled to an electronic control system 118 for information storage and processing. The tool 110 includes an elongated body 119 which encloses the downhole portion of the tool control system 116. The elongated body 119 may also carry a fluid admitting channel 120 and an extendable tool anchoring member 121 which are arranged on opposite sides of the elongated body 119. Admitted fluid flows through an analysis line 130, note FIG. 1B, and analysis cell 128. Radiation is passed through a switchable filter 126, the admitted fluid, and a reference channel of an analysis cell 128. Radiation detectors 132 measure the radiation after it has traversed the analysis cell. The use of an x-ray generating source 124, the filters 126, and radiation detectors 132 allow for the reliable determination of the density of the sample fluid in flow line 130. The module shown in FIG. 1B and described herein is useful as a standalone or integrated into a tool such as the MDT. Moreover, analysis of data generated from the device can take place downhole as a part of the module, or on the surface, for example, as a part of the electronic control system 118, or at a location that is remote from the wellsite.

X-ray tubes produce x-rays by accelerating electrons into a target via a high positive voltage difference between the target and electron source. The target is sufficiently thick to stop all the incident electrons. In the energy range of interest, the two mechanisms that contribute to the production of x-ray photons in the process of stopping the electrons are X-ray fluorescence and Bremsstrahlung radiation.

X-ray fluorescence radiation is the characteristic x-ray spectrum produced following the ejection of an electron from an atom. Incident electrons with kinetic energies greater than the binding energy of electrons in a target atom can transfer some (Compton Effect) or all (Photoelectric Effect) of the incident kinetic energy to one or more of the bound electrons in the target atoms thereby ejecting the electron from the atom.

If an electron is ejected from the innermost atomic shell (K-Shell), then characteristic K, L, M and other x-rays are produced. K x-rays are given off when an electron is inserted from a higher level shell into the K-Shell and are the most energetic fluorescence radiation given off by an atom. If an electron is ejected from an outer shell (L, M, etc.) then that type of x-ray is generated. In most cases, the L and M x-rays are so low in energy that they cannot penetrate the window of the x-ray tube. In order to eject these K-Shell electrons, an input of more than 80 kV is required in the case of a gold (Au) target due to their binding energy.

Another type of radiation is Bremsstrahlung radiation. This is produced during the deceleration of an electron in a strong electric field. An energetic electron entering a solid target encounters strong electric fields due to the other electrons present in the target. The incident electron is decelerated until it has lost all of its kinetic energy. A continuous photon energy spectrum is produced when summed over many decelerated electrons. The maximum photon energy is equal to the total kinetic energy of the energetic electron. The minimum photon energy in the observed Bremsstrahlung spectrum is that of photons just able to penetrate the window material of the x-ray tube.

The efficiency of converting the kinetic energy of the accelerated electrons into the production of photons is a function of the accelerating voltage. The mean energy per x-ray photon increases as the electron accelerating voltage increases.

The Bremsstrahlung spectrum from an x-ray tube operating at a fixed high voltage can be filtered to give predominantly a one peak spectrum. Specifically, a low pass filter will remove the higher energy portions of the radiation. Alternatively, a high pass filter will do the opposite, filtering out the lower end radiation. This is one feature relevant to the function of the invention as high and low energy measurements are required.

A Bremsstrahlung spectrum can be altered by changing (1) the composition of the filter, (2) the thickness of the filter, and (3) the operating voltage of the x-ray tube. The embodiments described herein utilize a dual filter mode to create low and high energy peaks from the same Bremsstrahlung spectrum using two different filters.

Figure 2:
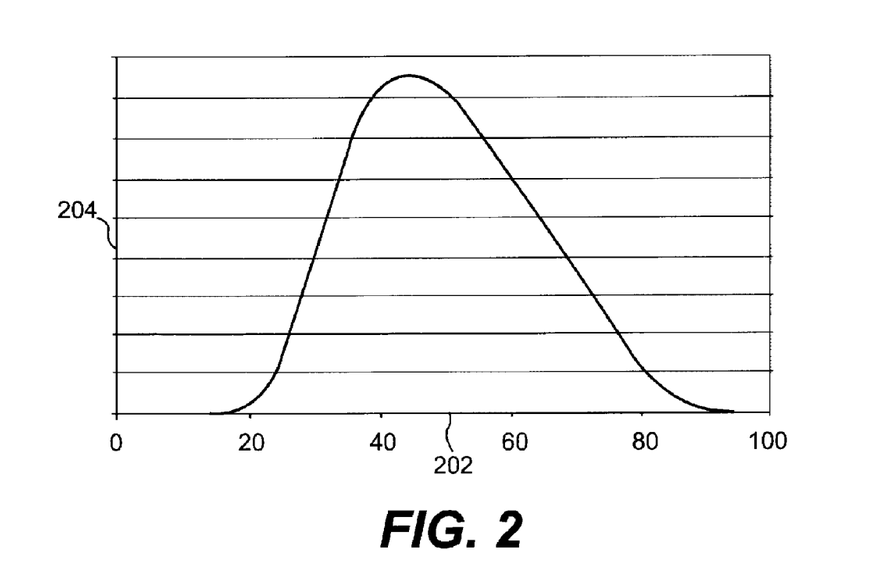
FIG. 2 is a graphic representation of a radiation energy spectrum output by an x-ray generator.

FIG. 2 shows the Bremsstrahlung radiation spectrum. Axis 202 is the energy measured in keV. Axis 204 is the count rate or the number of photons per second per keV that are incident on a radiation detector. This input radiation can be filtered using the low pass or high pass filters described above.

The density of a material can be determined by analyzing the attenuation of x-rays passed through the material. The initial measurement to be found is not the mass density, $\rho$, that will be the eventual product, but the electron density index, $\rho_e$, of the material. The electron density index is related to the mass density by the definition $$\rho_e = \frac{2 \cdot Z}{A} \rho.$$

The attenuation of a beam of x-rays of energy E, intensity $I_o(E)$, passing through a thickness d of material with a electron density index $\rho_e$ can be written $$I(E) = I_0(E) e^{\frac{\mu_m(E)\rho_e Ad}{2Z}}$$

where any interaction of the photons traversing the material attenuates the beam. Here, $\mu_m(E)$ is the mass coefficient of the material. I(E) in the previous equation does not include the detection of photons created following photoelectric absorption or multiple scattered photons.

Generating radiation using an x-ray generator to perform density measurement is desirable for a number of reasons. The radiation flux available and the need for photons with a quite low energy (<100 keV) make this type of radiation source well suited for the application. Measurement of the attenuation level is performed at two different mean energy levels: a high energy level (approximately 65 keV) where the photon attenuation occurs predominantly from Compton Scattering with some Photoelectric absorption and a low energy level (approximately 40 keV) where photon attenuation occurs from Compton Scattering and the Photoelectric Effect, where the absorption by the Photoelectric Effect is stronger than in the case of the high energy. Compton Scattering occurs when a photon "hits" an electron with some of the photon energy being transferred to the charged particle. The Photoelectric Effect is the emission of electrons from a material upon the absorption of electromagnetic radiation such as x-rays. In addition to the two energy levels, in order to have a robust measurement system, it is necessary to have a detection of radiation passing through a substance that will cause attenuation as well as a detection of radiation passing through air. The first of these is found by a measurement radiation detector and the second is found by a reference radiation detector.

Figure 3:
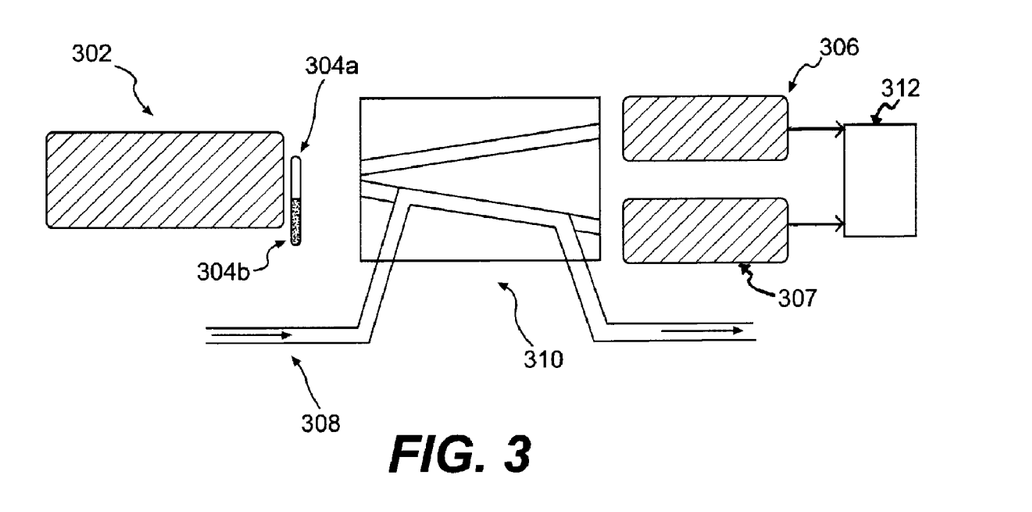
FIG. 3 is a schematic representation of one embodiment of the present disclosure.

Turning to FIG. 3, one embodiment of the x-ray fluid density measurement device is shown for implementation of the principles discussed herein. In this, the embodiment of FIG. 3 is adapted for operation at temperatures greater than 125° C. and in spatially constrained environments, such as typically found in oilfields. In one embodiment, the device may be one of a plurality of modules integrated into a downhole platform such as the exemplary one shown in FIG. 1A. X-ray generator 302 creates the Bremsstrahlung radiation spectrum shown in FIG. 2. In order to get the required system stability, the x-ray generator is operated at a constant accelerating voltage. A set of at least two filters is used. Filter 304a is a low pass filter positioned at the output of the x-ray generator 302 when a low energy measurement is desired. Filter 304b is a high pass filter positioned at the output of the x-ray generator 302 when a high energy measurement is desired. In one embodiment, the mean energy of the signal after filtering by the low pass filter is approximately 40 keV and the mean energy of the signal after filtering by the high pass filter is approximately 65 keV.

The radiation output from x-ray generator 302 is passed to sample cell 310. Radiation is then passed to the two radiation detectors 306 and 307. Channel 309 is a reference channel and passes radiation directly from the x-ray generator output (after filtering) to radiation detector 306, this will be the reference detector. The output of this reference radiation detector allows for normalization and a more accurate result. Channel 308 is a measurement channel. Formation fluid is pumped through this channel and the radiation passing through the channel also passes through the sample fluid. The radiation signal is attenuated by the fluid and this output radiation of the measurement channel 308 is passed to radiation detector 307. This radiation detector is referred to as the measurement detector. The measurement radiation detector and the reference radiation detector are placed symmetrically with respect to the x-ray generator 302. This ensures that a change in flux of the x-ray generator will be detected identically by radiation detectors 306 and 307. Data from the measurement radiation detector and the reference radiation detector may be passed to an analysis unit 312 for processing as described hereinafter.

Once the radiation measurements are obtained, it is necessary to account for the Z-effect before calculating the electron density index and ultimately the bulk density. This Z-effect is due to the Photoelectric Effect in attenuation of the radiation and is encountered because the energy of the x-rays used is relatively low. Because there is proportionally more Z-effect in the low energy than the high energy measurement, an estimate of the error due to the Z-effect in the high energy measurement can be determined by looking at the difference between the pair of attenuation measurements.

To do this, the previous equation is solved for the electron density index $$\rho_e = -S_1 \ln\left(\frac{I(E)}{I_0(E)}\right).$$

Where $S_1$ is equal to $$\frac{2Z}{d\mu_m(E)A}.$$

$I(E)$ corresponds to the output of the measurement radiation detector and this will be taken with a high pass filter ($M_{HE}$) and a low pass filter ($M_{LE}$). $I_o(E)$ is the output of the reference radiation detector. Again, this will be taken with a high pass filter ($R_{HE}$) and a low pass filter ($R_{LE}$). When taken, the ratios, $M_{HE}/R_{HE}$, $M_{LE}/R_{LE}$ will also be normalized by dividing them by the ratio found at the corresponding energy when just air is disposed between the x-ray generator and both radiation detectors.

Figure 4:
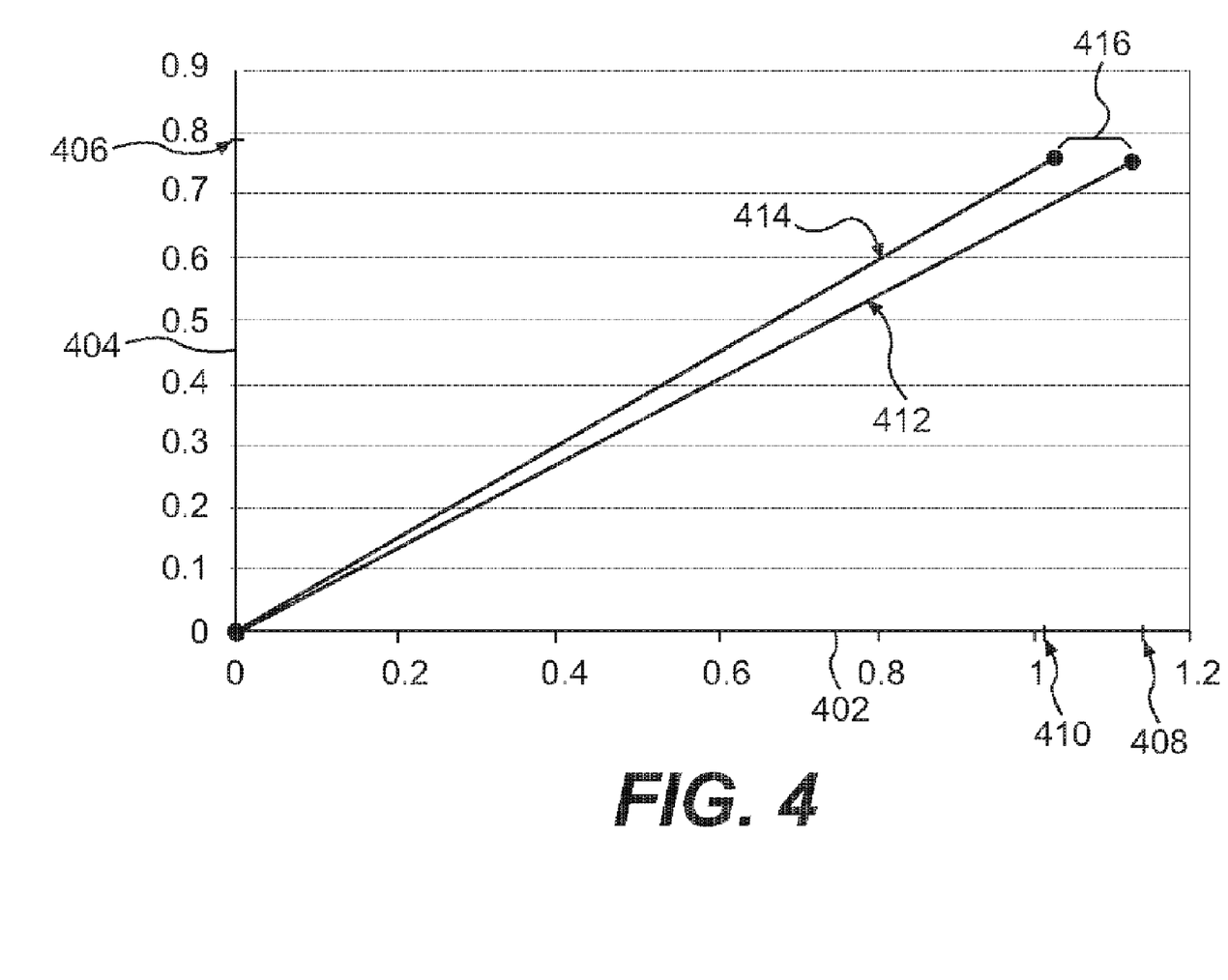
FIG. 4 is a graphic representation of the attenuation of hexane compared to its electron density.

The next step in the process of finding $\rho_e$ is to calibrate the system by inserting an attenuating material between the x-ray generator and the measurement radiation detector that has a known value of $\rho_e$. A hydrocarbon such as hexane is used so that the system will be calibrated to find a Z-effect value of pure hydrocarbons as zero so when measuring pure hydrocarbons, there will be no correction when determining $\rho_e$. Turning to FIG. 4, axis 402 is the value electron density index calculated from the equation above and labeled as the apparent electron density index. Axis 404 is actual electron density index. The electron density index of hexane is known to be 0.7635 in cgs units and is marked as element 406. The measurement and reference radiation detectors are first monitored with the low pass filter in place. This gives rise to a value for the apparent electron density index of the hexane at a low energy, or $\rho_{e,app,low}$. The same measurement is taken with a high pass filter in place to provide $\rho_{e,app,high}$. On axis 402, the value of $\rho_{e,app,low}$ is shown at 408 and the value of $\rho_{e,app,high}$ is shown at 410. By tracing from these points up to the known electron density index of hexane, two lines, 412 and 414 can be drawn to indicate the calibration gradients for high energy and low energy respectively. These two straight lines can then be used to determine the $\rho_{e,app,low}$ and $\rho_{e,app,high}$ for any material.

Figure 5:
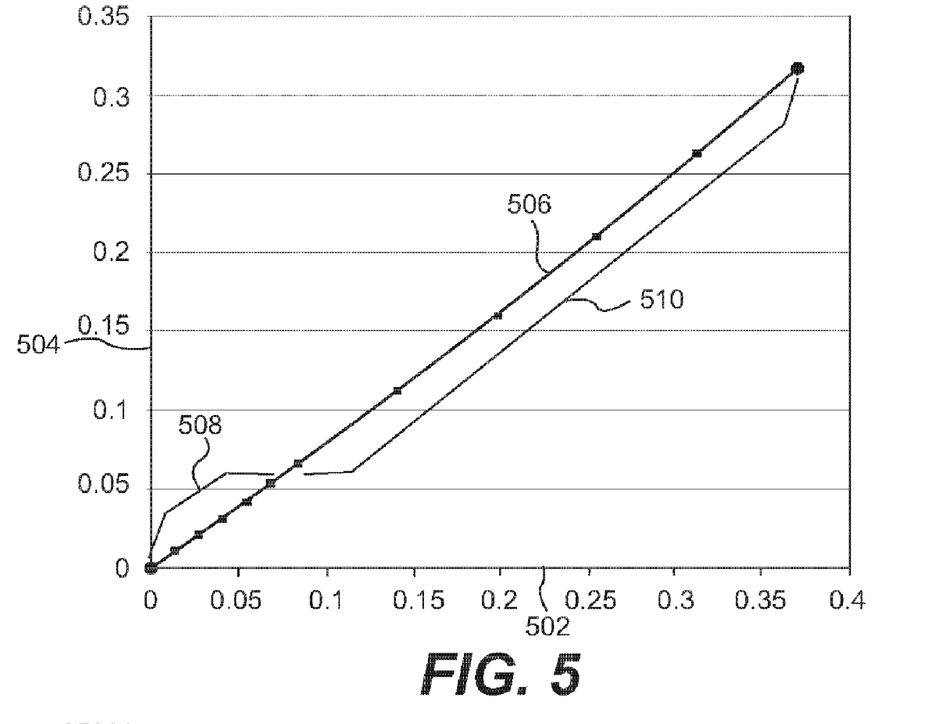
FIG. 5 is a graphic representation of a number of known substances for determining electron density.

The next step in the process is to correlate the difference between $\rho_{e,app,low}$ and $\rho_{e,app,high}$, or $\Delta\rho_{e,app}$ for a set of known materials and the difference between those materials' $\rho_{e,app,high}$ and their actual electron density index $\rho_{e,actual}$. Obviously, finding their $\rho_{e,actual}$ from this information is simple arithmetic. Turning to FIG. 5, this correlation is illustrated. Different concentrations of sulfur in oil and salt in water were used in generating this plot. This is because they exhibit a wide range of Z values and provide a large amount of information, also the difference between $\rho_{e,app,high}$ and their actual electron density index $\rho_{e,actual}$ is known. Axis 502 is the $\Delta\rho_{e,app}$ as measured from the two different gradients found in the method above. A plot point is then placed where these values intersect with the differences between $\rho_{e,app,high}$ and actual electron density index $\rho_{e,actual}$ shown on axis 504. The points in the range labeled 508 come from a sample of oil with sulfur, the points in the range 510 come from a sample of saltwater at different concentrations. Trace 506 is drawn through these plot points to reveal a nearly linear correlation that can be represented as $$\rho_{e,app,high} - \rho_{e,actual} = 0.306(\Delta\rho_{e,app})^2 + 0.7369(\Delta\rho_{e,app}).$$

In the case of an unknown material sample, all of this information can be determined to provide the $\rho_e$ of the material which can be converted to the mass density as described below.

Figure 6:
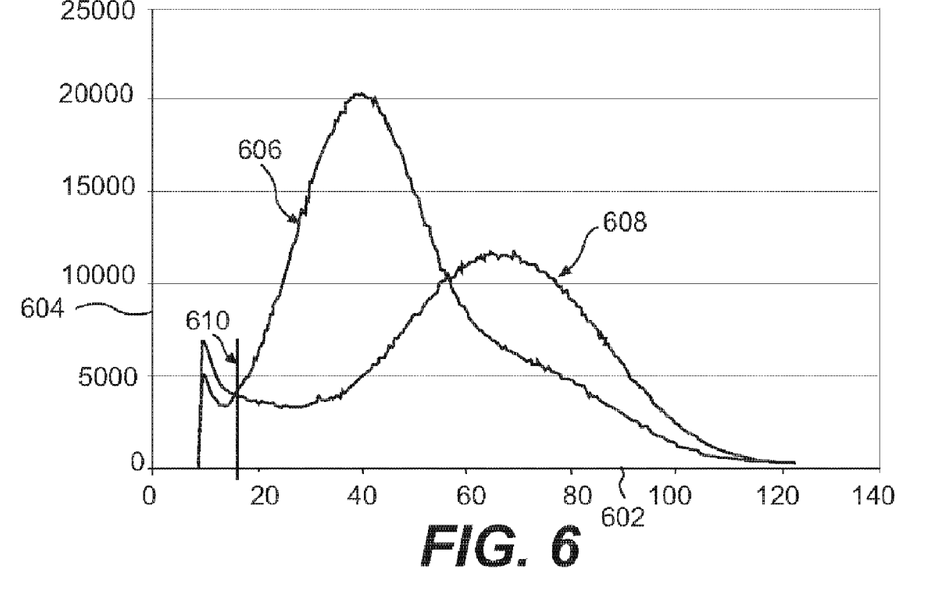
FIG. 6 is a graphic representation of a filtered radiation spectra used to measure fluid density.

The high pass filter used in one embodiment is a silver (Ag) filter. This provides an output x-ray with a mean energy of approximately 65 keV. The low pass filter in one embodiment is gadolinium (Gd) which provides a signal with a mean energy of around 42 keV. The spectra output by these filters is shown in FIG. 6. Axis 602 is energy in keV and axis 604 is the count rate detected by a radiation detector. Trace 606 represents the spectrum obtained when the input x-ray is filtered by a Gd filter. As described below, this allows for a low energy measurement with a peak at about 42 keV. Trace 608 represents the spectrum obtained with the input x-ray filtered by an Ag filter. Alternatively, this allows for a high energy measurement with a peak at approximately 65-70 keV.

The x-ray tube in one embodiment is operated at 80 kV because this is sufficiently high to make the two attenuation measurements at the different mean energies enabling the Z-effect correction described above while not requiring an excessively long x-ray tube. Filters could be chosen to provide a spectrum with a lower mean energy than 42 keV (as when using gadolinium) but lower energy spectra lead to problems in detecting certain elements. Specifically, the mean energy of the low energy filter output must be above the K-edge of barium. If not, the Z-effect correction detailed above will not work for barium, small quantities of which could exist in the mud filtrate during the initial formation fluid clean-up phase. For x-ray energies just below the K-edge of a particular element, that element causes much less attenuation. If the mean energy of the low energy beam were around 32 keV, the attenuation for barium for the low energy signal would be about the same as for the high energy signal, so the correction would be inaccurate.

For this reason, a Gd filter is chosen as the low pass filter in one embodiment. However, any filter can be used that provides a mean energy of approximately 40-50 keV. The K-edge of Gd is 47 keV creating a low energy peak with a mean energy of 42 keV, just above the K-edge of barium. This ensures that the low energy beam will be more attenuated by barium than the high energy beam and the correction for Z will be accurate in determining the electron density with up to 1% by weight of barium in the fluid.

The Ag filter was selected as the high pass filter in one embodiment, but any filter providing a mean energy of approximately 60-70 keV would be suitable. The K-edge of Ag (26 keV) is not used to modify the x-ray spectrum. The silver filter attenuates all the low energy x-rays below about 60 keV which effectively raises the mean energy of the transmitted signal to about 65 keV. The K-edge of the Ag filter does not cause any problems because there are no x-rays below 26 keV in the initial x-ray spectrum leaving the generator because of a 0.25 mm thick iron foil that is used to seal the x-ray generator housing.

Figure 7:
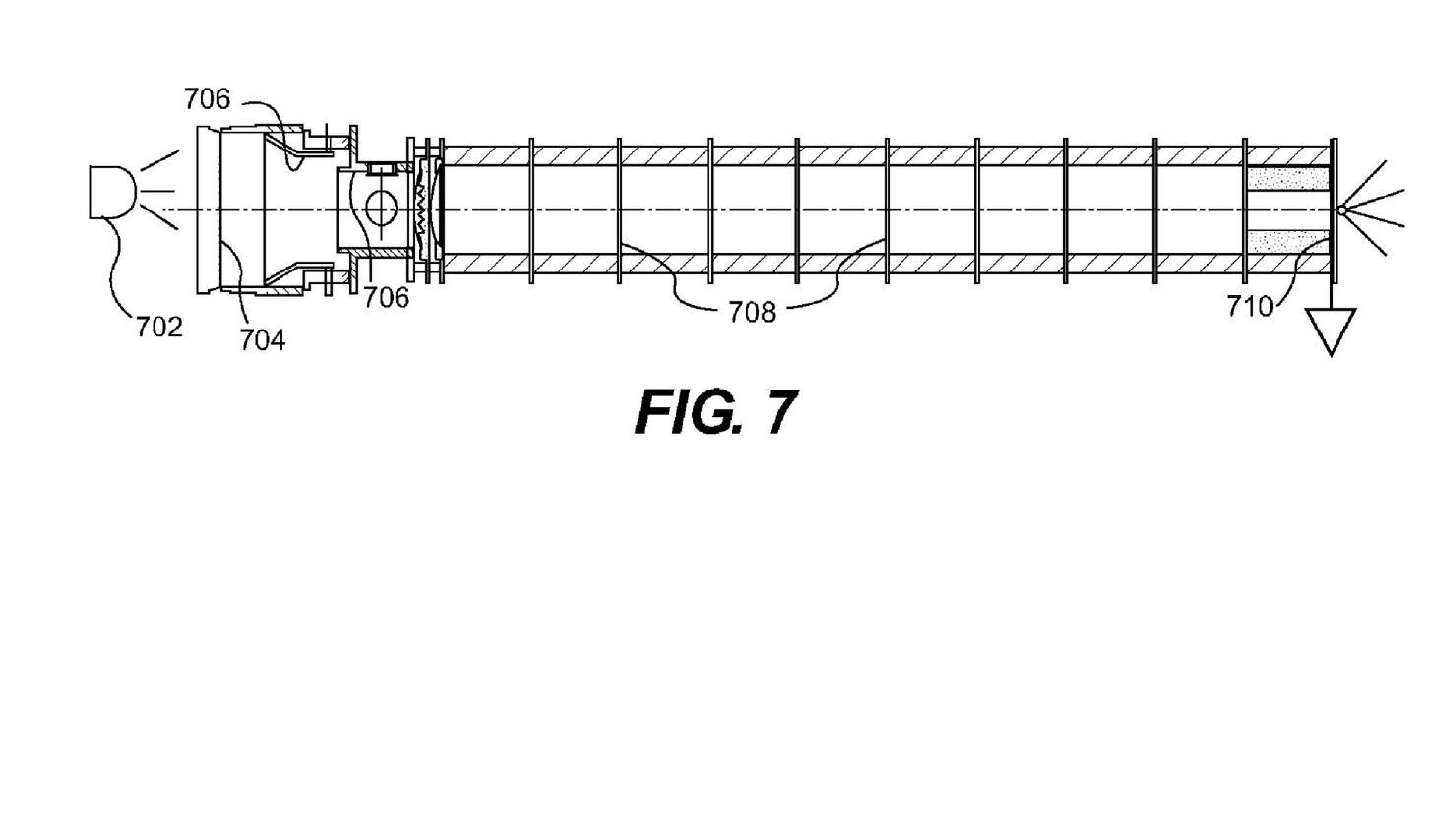
FIG. 7 is a schematic representation of one embodiment of an x-ray tube.

An example of an x-ray tube that may be used as an x-ray generator 302 is shown in FIG. 7. This particular x-ray tube is described in co-owned U.S. Pat. No. 5,680,431 entitled "X-Ray Generator", which is hereby incorporated by reference herein in its entirety. Light source 702 introduces light to photocathode 704. Photocathode 704 produces electrons in response to incident light. These electrons then proceed to the focusing electrodes 706 that route them on to the accelerating electrodes 708. These accelerating electrodes speed the electrons to target 710 to produce x-ray radiation as described above. In one embodiment, the x-ray tube is operated at a constant voltage of −80 kV on the photocathode. The x-ray tube has an internal collimator that allows the electron beam to hit a 2 mm diameter spot on a 5 micron thick gold (Au) target. Internal shielding allows only those x-rays generated in the Au target layer to exit the x-ray tube. These x-rays are then filtered by either filter 304a for a low energy measurement or filter 304b for a high energy measurement (note FIG. 3).

Figure 8:
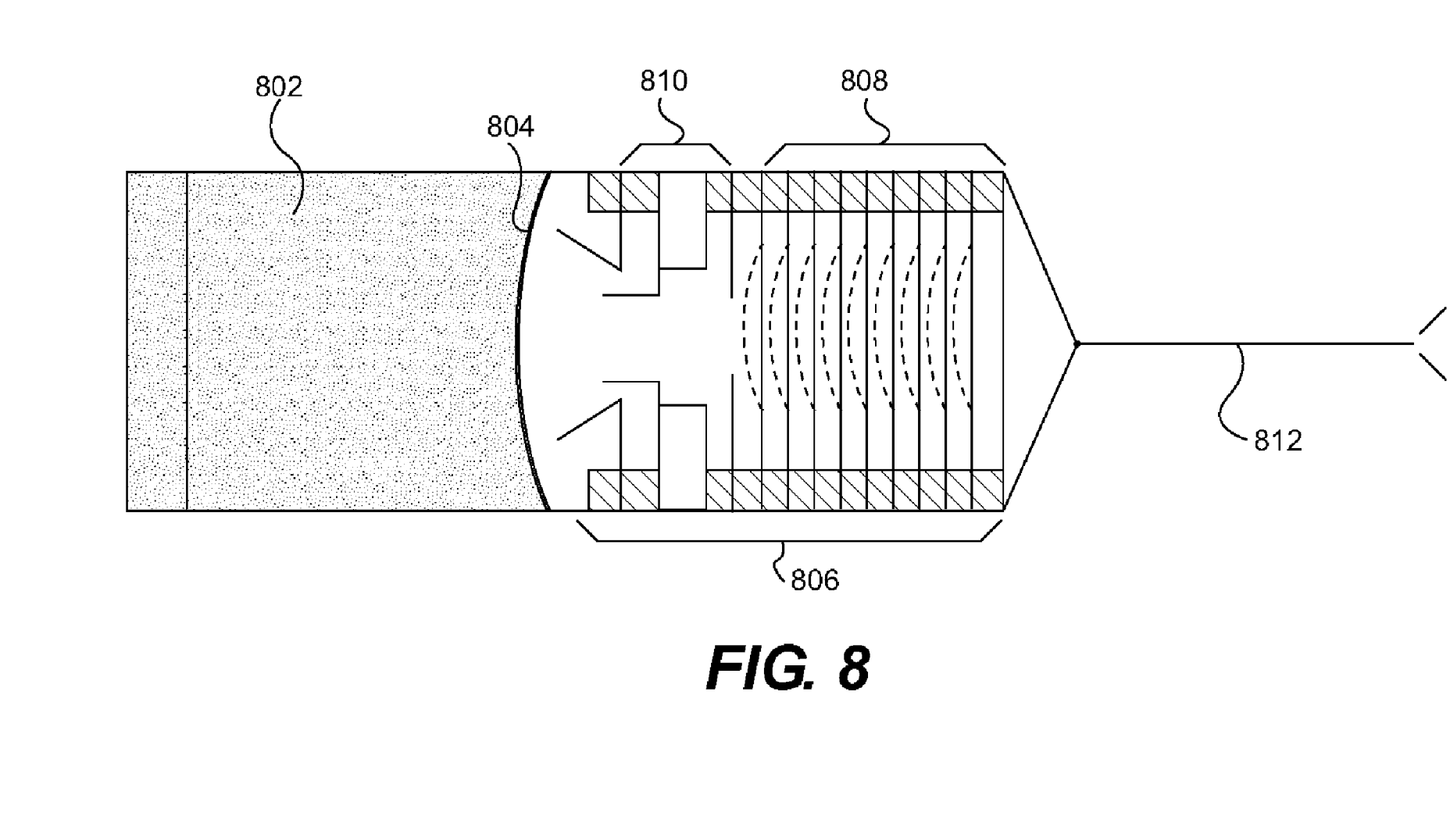
FIG. 8 is a schematic representation of a radiation detector used in one embodiment.

Turning to FIG. 8, an example of one type of radiation detector is shown that can be used as element 306. This radiation detector is further detailed in related co-owned U.S. patent application Ser. No. 11/312,841, which is hereby incorporated by reference herein in its entirety. Note that this is just one example of a radiation detector that may be used. Other types may be used provided they meet the space, noise, and temperature requirements encountered downhole. Radiation traveling through either the reference or measurement channel will collide with scintillating material 802. A scintillating material generates light when excited by incident radiation. The light then contacts photocathode 804 which generates an output of electrons proportional to the amount of light output by the scintillating material 802. These electrons are then routed by focus electrodes 810 to dynode stack 808. This dynode stack functions to multiply the electrons so that they can be measured as an electrical signal output on line 812. The focus electrodes and the dynode stack are referred to as an electron multiplier 806. The electrical signal output on line 812 will be proportional to the amount and intensity of radiation incident on the radiation detector. As would be expected, the radiation incident on the measurement detector will be attenuated in comparison to that on the reference detector. For applications requiring operation under extreme conditions of temperature and/or stability, one method of detecting x-rays is to use a scintillating material to convert some of the x-ray energy to light. The photomultiplier then acts as a low noise, high gain amplifier. Ceramic photomultipliers with hermetically sealed NaI(Tl) scintillator have been shown to be stable for 1000 s of hours at 150° C. Due to the scintillator properties, the probability that a given x-ray will interact to produce a light pulse is independent of temperature of the scintillator over the range of interest in the oilfield (−40 to 200° C.). However, the amplitude of the light output from the scintillator for a given x-ray and the gain of the photomultiplier may be affected by the temperature surrounding the detector. Thus, the number of pulses output from the photomultiplier is independent of temperature whereas the amplitudes of the output current signals for a detector operating at fixed high voltage change very significantly with temperature.

Due to these phenomena, a system that counts all the detector output pulses is nearly immune to temperature changes. This mode of operation is used here and is referred to as a plateau mode. In plateau mode, all the detector pulses of an energy level higher than a threshold are counted. The threshold is significantly higher than the thermionic noise of the system and significantly lower than the signal generated by the lowest energy x-ray that reaches the detector. In one embodiment, the threshold is the one shown in FIG. 6, element 610.

The ratio between the measurements of the measurement detector and the reference detector provides the normalized flux needed in calculation of electron density index. The output of each of the detectors is counted for a fixed time (1-30 seconds generally) with the filter 304a positioned at the output of the x-ray generator 302 and then with the filter 304b in position (note FIG. 3). This provides the low energy and high energy measurement, respectively. The high energy measurement at the reference detector is referred to as $R_{HE}$, the high energy measurement at the measurement detector is referred to as $M_{HE}$. The low energy measurements are referred to correspondingly as $R_{LE}$ and $M_{LE}$. These count rates are measured in counts/sec in this embodiment. Normally high energy and low energy count rates are monitored as fluids are drawn into the sample cell until no changes in the low energy and high energy count rates are observed in successive time intervals, then acquisition is started for the actual density determination. Thus, the expectation is that the density measurements will be made on non-varying samples and the density determination should be optimized for that case.

The determination of density from the information gathered proceeds as detailed in the equations and derivation above to determine an electron density index of the fluid sample. Once this is found, it is necessary to convert from an electron density index to a mass density to provide information that is of interest to the end customer or user.

There is a known correlation between electron density index and mass density $$\rho_e = 2\frac{Z}{A}\rho.$$

Where Z is the effective atomic number of the absorbing substance, A is its effective atomic weight, $\rho_e$ is the actual electron density index found in the description above, and $\rho$ is the mass density that is desired.

The $$2\frac{Z}{A}$$

portion of the equation is approximately equal to 1 for most elements with the notable exception of hydrogen where it is equal to 2. Since materials are being measured with varying weight fractions of hydrogen, it might appear, at first glance, that the weight fraction of hydrogen must be known for reliable measurements of the bulk density. In most cases, this weight fraction will not be available.

In order to find the correct mass density of the materials, a graph is made plotting the $\rho_e$ of several known materials against their mass density. This plot reveals a nearly linear relationship that yields a correlation between electron density index and mass density as follows $$\rho = 0.1192\rho_e^2 + 0.77\rho_e.$$

This equation fits nearly all data points with a high accuracy. This alleviates the need to know the weight fraction of hydrogen in all but the heaviest hydrocarbons. For all practical conditions in the field, this will provide a reliable determination of the mass density.

Figure 9:
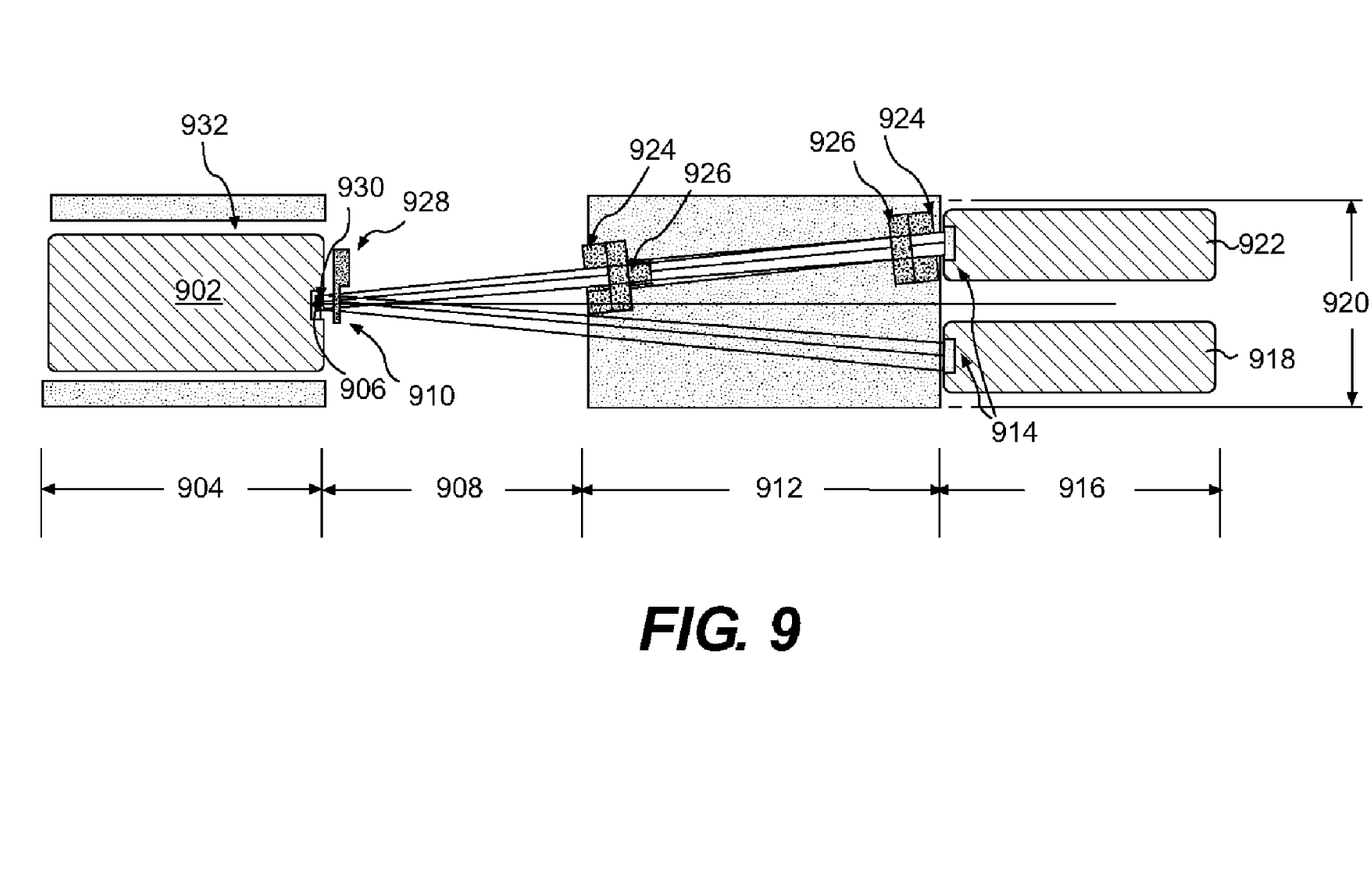
FIG. 9 is a schematic representation of physical dimensions of one embodiment of the current disclosure.

As noted above, the density detection device described herein is operable in the extreme conditions experienced downhole where the ambient temperature may reach 200° C. In addition to this high temperature tolerance, the device fits into a highly restricted space. As part of the exemplary modular tool shown in FIG. 1, the density determination device will only be afforded a limited amount of space that must be used economically. FIG. 9 shows one embodiment that meets all of the space limitations. X-ray generator 902 is bordered by walls 903 and 905. Shock absorbing gel 932 surrounds the x-ray generator to protect it from shock and vibration that are common downhole. X-ray target 906 is constructed of Au and is about 5.1 mm in width. A 0.25 mm layer 930 of Kovar is positioned between the target 906 and the filters. Element 910 is a 0.5 mm Ag filter for use in obtaining the high energy measurement, filter 928 is the 0.5 mm Gd filter used in obtaining the low energy measurement. The x-ray radiation signal leaving the filter then proceeds through measurement channel 911 and reference channel 913. Steel locking ring 924 is 10 mm thick and holds the 10 mm thick boron carbide window 926 in place. At the output of these channels, the radiation passes through element 914, a 12 mm crystal diameter. Measurement detector 922 and reference detector 918 monitor the output radiation and produce information used in the calculation of fluid density.

X-ray generator section 904 in this embodiment is 12" long. The space 908 between the x-ray generator 902 and the sample cell is 3.5". The sample cell section 912 is 5" long and the detector section 916 is 4" in length. The width 920 of the device is 3". The full dimensions of the device in this embodiment are 24.5" long and 3" wide. This is suitable for use in a modular tool in the downhole environment.

The x-ray density measurement can be taken in the borehole in a number of ways. In a borehole that has previously been drilled, the device can operate downhole on a wireline device such as the one shown in FIG. 1. Alternatively, the device can operate for logging while drilling implementations. Other possible implementations include measurement-while-drilling (MWD), production logging, and permanent monitoring of oilfield type tools and in connection with oilfield hardware such as pipelines. Analysis of the data from the device can take place downhole as a part of the module, or on the surface. If the analysis is completed on the surface, suitable telemetry is used to convey signals from the device to an analysis module.

The preceding description has been presented only to illustrate and describe the invention and some examples of its implementation. It is not intended to be exhaustive or to limit the invention to any precise form disclosed. Many modifications and variations are possible and would be envisioned by one of ordinary skill in the art in light of the above teaching. One such modification obvious to those skilled in the art is to use the Z effect measurement described in the above to provide information about the average Z of the sample material or the size of the contribution from the Photoelectric Effect.

The various aspects were chosen and described in order to best explain principles of the invention and its practical applications. The preceding description is intended to enable others skilled in the art to best utilize the invention in various embodiments and aspects and with various modifications as are suited to the particular use contemplated. It is intended that the scope of the invention be defined by the following claims; however, it is not intended that any order be presumed by the sequence of steps recited in the method claims unless a specific order is directly recited.

What is claimed is:

1. A tool for downhole analysis comprising:
   an X-ray generator configured to emit a high energy radiation signal and a low energy radiation signal;
   a sample cell operably connected to said x-ray generator and configured to house a sample of interest and to direct at least one of said high energy and said low energy radiation signals through said sample cell; and a radiation detector operably connected to said sample cell being configured to measure the output radiation from said sample cell, wherein said radiation detector is operable to provide an output signal for determination of mass density of said sample of interest using:

$$\rho = C_3 \rho_e^2 + C_4 \rho_e$$

where $\rho$ is mass density, $\rho_e$ is electron density index, and $C_3$ and $C_4$ are calibration coefficients relating the electron density index of the material to the mass density.

2. The tool for downhole analysis as defined in claim 1, further comprising:

a filter mechanism operably connected to said x-ray generator and positioned at an output of said x-ray generator, said filter mechanism comprising a low pass filter and a high pass filter and being configured to produce said high energy radiation signal and said low energy radiation signal.

3. The fluid density determination apparatus as defined in claim 2, wherein:

one of said filters is a low energy bandpass filter.

4. The fluid density determination apparatus as defined in claim 3 wherein said low energy bandpass filter comprises gadolinium (Gd).

5. The tool for downhole analysis as defined in claim 1, wherein:

said sample of interest is formation fluid.

6. The fluid density determination apparatus as defined in claim 2, wherein: one of said filters is a high energy pass filter.

7. The fluid density determination apparatus as defined in claim 6 wherein:

said high energy pass filter comprises silver (Ag).

8. The tool for downhole analysis as defined in claim 1, wherein:

said radiation detector is operable for detecting radiation that has passed through said sample of interest.

9. The tool for downhole analysis as defined in claim 1, further comprising:

a reference radiation detector.

10. The fluid density determination apparatus as defined in claim 9, wherein:

said measurement radiation detector and said reference radiation detector are positioned symmetrically with respect to said X-ray generator.

11. The tool for downhole analysis as defined in claim 1, wherein:

said tool is configured to operate at temperatures greater than or equal to 125° C.

12. The fluid density determination apparatus as defined in claim 1, wherein:

said radiation detector determines an amount of incident radiation over a given time period.

13. The fluid density determination apparatus as defined in claim 1, wherein:

said apparatus is configured for operation downhole in a well traversing a formation.

14. The fluid density determination apparatus as defined in claim 13, wherein:

said test material is formation fluid.

15. The fluid density determination apparatus as defined in claim 1, wherein:

said apparatus is one module of a plurality of modules integrated into a modular analysis device.

16. The fluid density determination apparatus as defined in claim 1, wherein:

said apparatus being configured to operate at temperatures greater than or equal to 125° C.

17. The fluid density determination apparatus as defined in claim 1, wherein:

said radiation has an energy lower than or equal to 100 keV.

18. The fluid density determination apparatus as defined in claim 1, wherein:

said analysis is performed while drilling.

19. The fluid density determination apparatus as defined in claim 1, wherein:

said analysis is performed separately from drilling.

20. The fluid density determination apparatus as defined in claim 1, wherein:

said analysis unit operates at the surface.

21. The fluid density determination apparatus as defined in claim 1, wherein:

said analysis unit operates in a borehole.

22. A method for determining density of a fluid in a high temperature environment comprising:

(a) producing radiation in response to an input voltage using an X-ray generator;

(b) filtering said radiation at an output of said X-ray generator using at least two filters that are alternately disposed at said output to produce a filtered radiation signal;

(c) channeling said filtered radiation signal through an analysis cell comprising a first channel and a second channel wherein a test material is inserted into said first channel;

(d) detecting radiation at an output of said first channel using a measurement radiation detector wherein the radiation detected by said measurement radiation detector has passed through said test material;

(e) detecting radiation at an output of said second channel using a reference radiation detector wherein the radiation detected by said reference radiation detector has not passed through said test material; and (f) calculating a mass density of said test material based on information gathered by said reference radiation detector and said measurement radiation detector including calculating an electron density index of said test material and further comprising a set of calibration steps to determine said electron density index, said calibration steps comprising;

using a calibration material with a known electron density index as said test material;

determining an attenuation due to said calibration material at a high energy and a low energy;

plotting said high energy attenuation and said low energy attenuation against said known electron density index to create two points;

drawing a high energy calibration curve and a low energy calibration curve from an origin (0,0) to said high energy attenuation and said low energy attenuation points;

inserting a plurality of known mixtures with known electron density indexes;

determining an apparent electron density index at a high energy and at a low energy for each of said plurality of known mixtures by utilizing said calibration curves;

plotting a plurality of correlation points representing the difference between the low energy and high energy apparent electron density indexes against the difference between the high energy apparent electron density index and the true electron density index for each of the known mixtures; and generating a correlation equation for the curve extending through said correlation points, wherein said correlation equation is of the form:

$$\rho_{e,app,high} - \rho_{e,actual} = C_1(\Delta\rho_{e,app})^2 + C_2(\Delta\rho_{e,app})$$

where $C_1$ and $C_2$ are correlation coefficients.

23. A method for determining density of a fluid in a high temperature environment comprising:
   (a) producing radiation in response to an input voltage using an X-ray generator;
   (b) filtering said radiation at an output of said X-ray generator using at least two filters that are alternately disposed at said output to produce a filtered radiation signal;
   (c) channeling said filtered radiation signal through an analysis cell comprising a first channel and a second channel wherein a test material is inserted into said first channel;
   (d) detecting radiation at an output of said first channel using a measurement radiation detector;
   (e) detecting radiation at an output of said second channel using a reference radiation detector; and
   (f) calculating a mass density of said test material based on information gathered by said reference radiation detector and said measurement radiation detector,
   wherein calculating a mass density of said test material comprises calculating an electron density index of said test material.

24. The method for determining density of a fluid in a high temperature environment as defined in claim 23 further comprising:
   a set of calibration steps to determine said electron density index.

25. The method for determining density of a fluid in a high temperature environment as defined in claim 24 wherein:
   said calibration steps comprise:
   using a calibration material with a known electron density index as said test material;
   determining an attenuation due to said calibration material at a high energy and a low energy;
   plotting said high energy attenuation and said low energy attenuation against said known electron density index to create two points;
   drawing a high energy calibration curve and a low energy calibration curve from an origin (0,0) to said high energy attenuation and said low energy attenuation points;
   inserting a plurality of known mixtures with known electron density indexes;
   determining an apparent electron density index at a high energy and at a low energy for each of said plurality of known mixtures by utilizing said calibration curves;
   plotting a plurality of correlation points representing the difference between the low energy and high energy apparent electron density indexes against the difference between the high energy apparent electron density index and the true electron density index for each of the known mixtures;
   generating a correlation equation for the curve extending through said correlation points.

26. The method for determining density of a fluid in a high temperature environment as defined in claim 25 further comprising:
   inserting an unknown material as said test material; determining a high energy attenuation and a low energy attenuation for said unknown material;
   determining the electron density index of said unknown material using said correlation equation.

27. The method for determining density of a fluid in a high temperature environment as defined in claim 25 wherein:
   the electron density index of said test material is calculated using a correlation equation of the form:

$$\rho_{e,app,high} - \rho_{e,actual} = C_1(\Delta\rho_{e,app})^2 + C_2(\Delta\rho_{e,app})$$

where $C_1$ and $C_2$ are correlation coefficients.

28. A method for determining density of a fluid in a high temperature environment comprising:
   (a) producing radiation in response to an input voltage using an X-ray generator;
   (b) filtering said radiation at an output of said X-ray generator using at least two filters that are alternately disposed at said output to produce a filtered radiation signal;
   (c) channeling said filtered radiation signal through an analysis cell comprising a first channel and a second channel wherein a test material is inserted into said first channel;
   (d) detecting radiation at an output of said first channel using a measurement radiation detector;
   (e) detecting radiation at an output of said second channel using a reference radiation detector; and
   (f) calculating a mass density of said test material based on information gathered by said reference radiation detector and said measurement radiation detector, wherein said mass density is calculated using an electron density index according to the following formula:

$$\rho = C_3\rho_e^2 + C_4\rho_e$$

where $C_3$ and $C_4$ are calibration coefficients relating the electron density index of the material to the mass density.

29. The method for determining the density of a fluid in a high temperature environment as defined in claim 28, wherein:
   said filtering comprises filtering out a high energy portion of the radiation to create a low energy signal.

30. The method for determining density of a fluid in a high temperature environment as defined in claim 29 further comprising:
   determining an amount of incident radiation over time by said measurement radiation detector and said reference radiation detector.

31. The method for determining density of a fluid in a high temperature environment as defined in claim 28, wherein:
   said filtering comprises filtering out a low energy portion of the radiation to create a high energy signal.

32. The method for determining density of a fluid in a high temperature environment as defined in claim 31 further comprising:
   determining an amount of incident radiation over time by said measurement radiation detector and said reference radiation detector.

33. The method for determining density of a fluid in a high temperature environment as defined in claim 28 further comprising:
   positioning said filters symmetrically with respect to said X-ray generator.

* * * * *